US011255182B2

(12) United States Patent
Hai et al.

(10) Patent No.: US 11,255,182 B2
(45) Date of Patent: Feb. 22, 2022

(54) METHOD AND APPARATUS FOR DETERMINING OIL-GAS-WATER INTERFACE BASED ON FORMATION PRESSURE EQUIVALENT DENSITY

(71) Applicant: PetroChina Company Limited, Beijing (CN)

(72) Inventors: Chuan Hai, Beijing (CN); Chengwen Xiao, Beijing (CN); Qiang Chen, Beijing (CN); Shengqiang Zhang, Beijing (CN); Zhenyuan Luo, Beijing (CN); Peng Liu, Beijing (CN); Ni Liu, Beijing (CN); Hongbo Guo, Beijing (CN)

(73) Assignee: PETROCHINA COMPANY LIMITED, Beijing (CN)

( * ) Notice: Subject to any disclaimer, the term of this patent is extended or adjusted under 35 U.S.C. 154(b) by 55 days.

(21) Appl. No.: 16/830,723

(22) Filed: Mar. 26, 2020

(65) Prior Publication Data

US 2021/0010368 A1 Jan. 14, 2021

(30) Foreign Application Priority Data

Jul. 12, 2019 (CN) .......................... 201910627783.9

(51) Int. Cl.
*E21B 47/047* (2012.01)
*E21B 47/06* (2012.01)
(Continued)

(52) U.S. Cl.
CPC .......... *E21B 47/047* (2020.05); *E21B 47/022* (2013.01); *E21B 47/06* (2013.01);
(Continued)

(58) Field of Classification Search
CPC ....... E21B 47/047; E21B 47/06; E21B 47/022
See application file for complete search history.

(56) References Cited

U.S. PATENT DOCUMENTS 4,282,750 A * 8/1981 Prats ....................... E21B 49/10
73/152.39
6,182,013 B1 1/2001 Malinverno et al.
(Continued)

FOREIGN PATENT DOCUMENTS

CN 104568052 A 4/2015
CN 105550773 A 5/2016
(Continued)

OTHER PUBLICATIONS

Luo, Xingping et al. "A Method of Determining Oilgaswater Interface by MDT Single Pressure Data Point", Well Logging Technology, vol. 35 No. 2, Apr. 2011, pp. 180-182.
(Continued)

*Primary Examiner* — Catherine Loikith
(74) *Attorney, Agent, or Firm* — Loza & Loza, LLP; Michael F. Fedrick

(57) ABSTRACT

A method for determining an oil-gas-water interface based on the formation pressure equivalent density. The method comprising: determining working parameters of the wireline modular formation tester based on the acquired conventional logging data of a block to be studied; acquiring a series of formation pressure and corresponding depth data based on the working parameter; computing formation pressure equivalent densities at different depths based on the formation pressure and the corresponding depth data; drawing a crossplot of the formation pressure equivalent density and the depth according to the formation pressure equivalent density and the corresponding depth data at the different depths; and determining the oil-gas-water interface according to the position of breaking point of the formation pressure equivalent density on the crossplot of the formation pressure equivalent density and the depth.

14 Claims, 7 Drawing Sheets

(51) Int. Cl.
*E21B 47/022* (2012.01)
*G01V 9/00* (2006.01)
*G01N 33/28* (2006.01)
*E21B 43/26* (2006.01)
*E21B 43/11* (2006.01)

(52) U.S. Cl.
CPC ........... *G01N 33/2823* (2013.01); *G01V 9/00* (2013.01); *E21B 43/11* (2013.01); *E21B 43/26* (2013.01)

(56) References Cited

U.S. PATENT DOCUMENTS

| | | | | |
|---|---|---|---|---|
| 6,609,568 B2 * | 8/2003 | Krueger | ................ | E21B 47/06 166/250.07 |
| 7,472,594 B1 * | 1/2009 | Davies | ................ | G01K 11/32 73/295 |
| 7,731,421 B2 * | 6/2010 | Hadley | ................ | E21B 47/047 374/136 |
| 8,180,602 B2 * | 5/2012 | Barboza | ................ | E21B 49/00 703/2 |
| 9,574,433 B2 * | 2/2017 | Bennett | ................ | G01V 11/00 |
| 2015/0083495 A1 * | 3/2015 | Walker | ................ | E21B 7/04 175/50 |

FOREIGN PATENT DOCUMENTS

CN 107288618 A 10/2017
EA 027715 B 8/2017

OTHER PUBLICATIONS

Search Report prepared by the China Patent Information Center dated Jun. 14, 2019.

* cited by examiner

METHOD AND APPARATUS FOR DETERMINING OIL-GAS-WATER INTERFACE BASED ON FORMATION PRESSURE EQUIVALENT DENSITY

CROSS REFERENCE TO RELATED APPLICATIONS

This application claims the benefit of priority from Chinese Patent Application Number 201910627783.9, entitled "Method and Apparatus for Determining Oil-Gas-Water Interface Based on Formation Pressure Equivalent Density", filed on Jul. 12, 2019, the subject matter of which is incorporated herein by reference.

TECHNICAL FIELD

The invention relates to the technical field of oil and gas exploration of a clastic rock reservoir, in particular to a method and an apparatus for determining an oil-gas-water interface based on a formation pressure equivalent density.

BACKGROUND

According to the buoyancy principle, oil gas or other fluids with a density lower than the water density of the surrounding formation in the formation will be subjected to the buoyancy and tend to be moved from underground to the ground surface. Due to existence of geological structures such as anticlines, oil gas or carbon dioxide will accumulate at the top of the geological structures to form oil and gas reservoirs or carbon dioxide gas reservoirs, and the like. This creates an additional pressure on the inner top surface of the geological structure, and the magnitude of the additional pressure is related to a density difference between the reservoir-forming fluid and the formation water as well as the reservoir-forming height, as shown in FIG. 1. It is found through research that such a buoyancy effect can be reflected by the law that the formation pressure equivalent density in oil and gas reservoirs changes with depth. The formation pressure equivalent density Q (also referred to as a formation pressure coefficient in some papers) refers to a fluid density to generate the same formation pressure of a fluid column whose height is the formation depth under hydrostatic conditions. The calculation formula thereof is that the formation pressure at this depth is divided by a vertical depth and then by a coefficient. The value of the coefficient depends on whether the formation pressure is in the unit of MPa or PSI (pounds per square inch). Q is mainly used in the oilfield to determine mud density in the well, so as to balance the formation pressure and ensure that the safety of drilling engineering in easy-to-spray and easy-to-leak formations. However, based on the buoyancy effect principle of oil and gas reservoirs, the method of identifying and dividing oil and gas reservoirs by the relationship between Q and depth variation has not been reported.

SUMMARY OF THE INVENTION

Embodiments of the present invention provide a method and an apparatus for determining the oil-gas-water interface based on the formation pressure equivalent density, which solve difficulty in identification of the oil-gas-water layer of low resistivity oil reservoir, heavy oil reservoir, and low porosity and low permeability oil and gas reservoir.

An embodiment of the present invention provides a method for determining the oil-gas-water interface based on the formation pressure equivalent density, comprising:
acquiring conventional logging data of an oilfield to be studied;
analyzing the conventional logging data and determining the working parameters of the wireline modular formation tester;
acquiring a series of formation pressure and corresponding depth data, wherein the formation pressure and the corresponding depth data are obtained by the wireline modular formation tester performing a test under the working parameters;
computing formation pressure equivalent densities at different depths according to the formation pressure and the corresponding depth data;
drawing a crossplot of the formation pressure equivalent density and the depth according to the formation pressure equivalent density and the corresponding depth data at different depths; and
determining the oil-gas-water interface according to the position of the breaking point of the formation pressure equivalent density on the crossplot of the formation pressure equivalent density and the depth.

Embodiments of the present invention also provide a computer-readable storage medium which stores a computer program for implementing the following steps of:
acquiring conventional logging data of an oilfield to be studied;
analyzing the conventional logging data and determining the working parameters of the wireline modular formation tester;
acquiring a series of formation pressure and corresponding depth data, wherein the formation pressure and the corresponding depth data are obtained by the wireline modular formation tester performing a test under the working parameter;
computing formation pressure equivalent densities at different depths according to the formation pressure and the corresponding depth data;
drawing a crossplot of the formation pressure equivalent density and the depth according to the formation pressure equivalent density and the corresponding depth data at the different depths; and
determining the oil-gas-water interface according to the position of the breaking points of the formation pressure equivalent density on the crossplot of the formation pressure equivalent density and the depth.

In the embodiments of the present invention, the formation pressure equivalent densities at different depths are determined through the formation pressure and corresponding depth data in the logging data of the wireline modular formation tester, then a crossplot of the formation pressure equivalent density and the depth is drawn according to the formation pressure equivalent density and the corresponding depth data at the different depths, and the oil-gas-water interfaces are determined according to the position of the breaking points of the formation pressure equivalent density on the crossplot of the formation pressure equivalent density and the depth. In this way the accuracy of identification of low resistivity reservoir, heavy oil reservoir, and low porosity and low permeability oil and gas reservoir can be improved, division of the oil-gas-water layer is more accurate, so as to provide a scientific basis for the deployment and planning of oil and gas exploration schemes.

BRIEF DESCRIPTION OF THE DRAWINGS

In order to more clearly explain the embodiments of the invention or the technical solution in the prior art, drawings that need to be used in the description in embodiments or the prior art will be simply introduced below, obviously the drawings in the following description are merely some examples of the invention, for persons ordinarily skilled in the art, it is also possible to obtain other drawings according to these drawings without making creative efforts.

DETAILED DESCRIPTION OF THE PREFERRED EMBODIMENTS

Hereinafter the technical solution in the embodiments of the present invention will be described clearly and integrally in combination with the accompanying drawings in the embodiments of the present invention, and obviously the described embodiments are merely parts of the embodiments, rather than all of the embodiments. Based on the embodiments of the present invention, all other embodiments that are obtained by persons skilled in the art without making creative efforts fall within the protection scope of the present invention.

Figure 1:
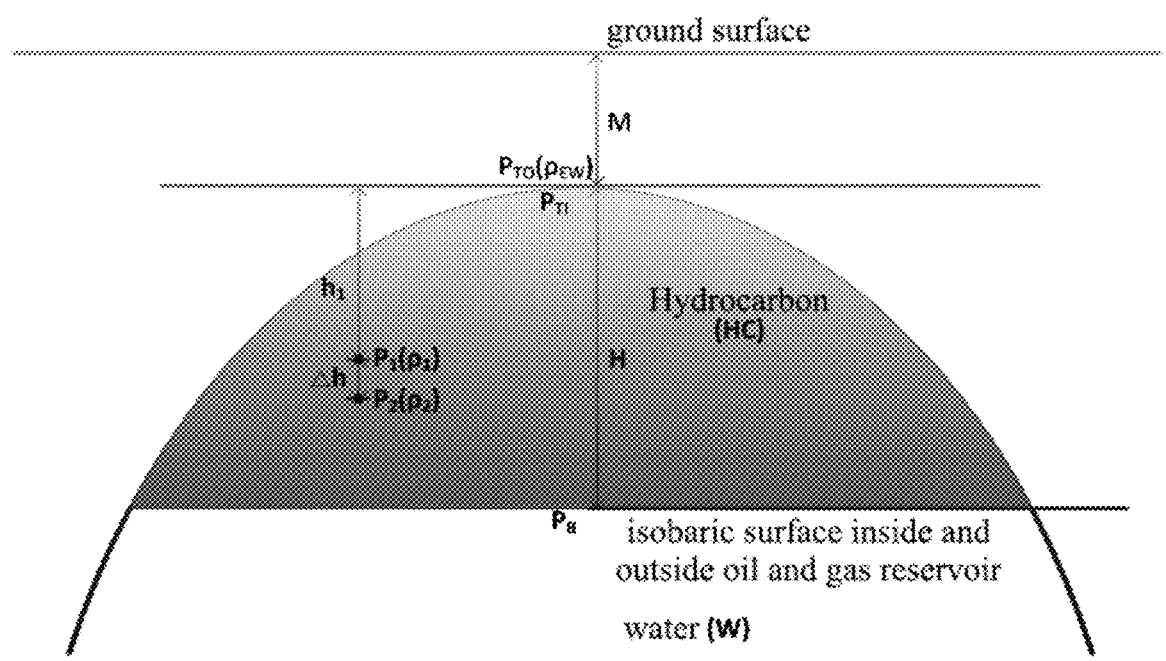
FIG. 1 is a schematic diagram of an anticlinal oil and gas reservoir.
Figure 2:
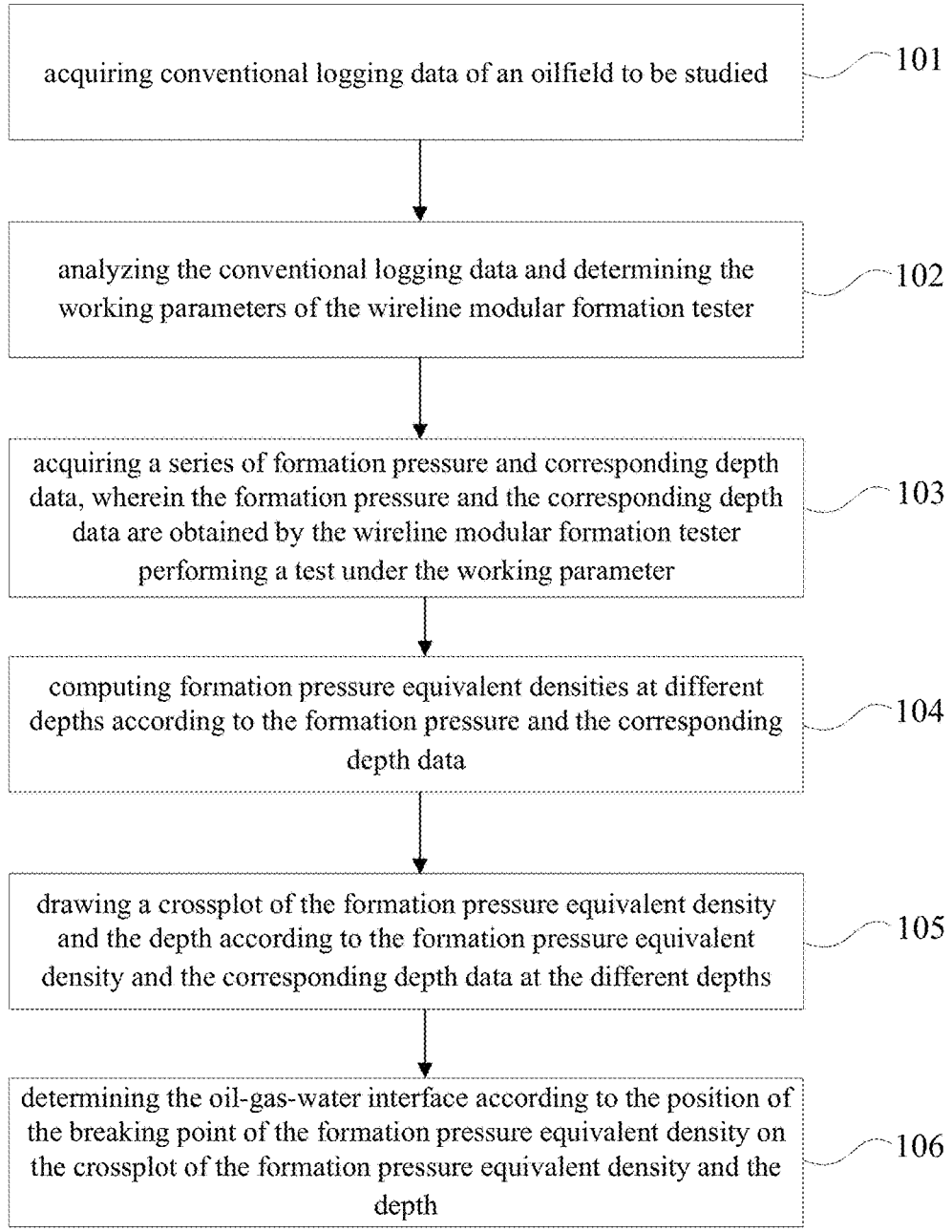
FIG. 2 is a flowchart (1) of a method for determining the oil-gas-water interface based on the formation pressure equivalent density provided in an embodiment of the present invention.

In the embodiments of the present invention, a method for determining the oil-gas-water interface based on the formation pressure equivalent density is provided, as shown in FIG. 2, the method comprises:

step 101: acquiring conventional logging data of an oilfield to be studied;

step 102: analyzing the conventional logging data and determining the working parameters of the wireline modular formation tester;

step 103: acquiring a series of formation pressure and corresponding depth data, wherein the formation pressure and the corresponding depth data are obtained by the wireline modular formation tester performing a test under the working parameter;

step 104: computing formation pressure equivalent densities at different depths according to the formation pressure and the corresponding depth data;

step 105: drawing a crossplot of the formation pressure equivalent density and the depth according to the formation pressure equivalent density and the corresponding depth data at the different depths;

step 106: determining the oil-gas-water interface according to the position of the breaking point of the formation pressure equivalent density on the crossplot of the formation pressure equivalent density and the depth.

In the embodiments of the present invention, in step 101 to step 103, the acquired conventional logging data of an oilfield to be studied may include: the natural gamma, natural potential and caliper curves that describe formation lithology and borehole environment; the P-wave slowness, density and neutron curves that reflect formation physical properties; and several resistivity curves that reflects fluid properties within the pores of the formation. Based on the analysis of the conventional logging data, the number of points of measuring formation pressure and related depth locations in a suspected reservoir section (a reservoir section where the reservoir fluid properties cannot be determined using the conventional logging data) need to be determined, then an instruction is formed accordingly and sent to the wireline modular formation tester at a logging site which performs corresponding operations, and the wireline modular formation tester is monitored to measure the qualified data (i.e. formation pressure and corresponding depth data) according to the technical specifications. The depth points to be measured at key locations should be fine-tuned to ensure that high-quality data can be obtained.

In the embodiments of the present invention, since the logging depth is recorded by lowering the wireline from zero value of the kelly bushing of the drilling platform, it is necessary to perform a vertical depth correction on the logging depth in wells with a well inclination greater than 3 degrees, so as to convert the logging depth into the vertical depth.

Figure 3:
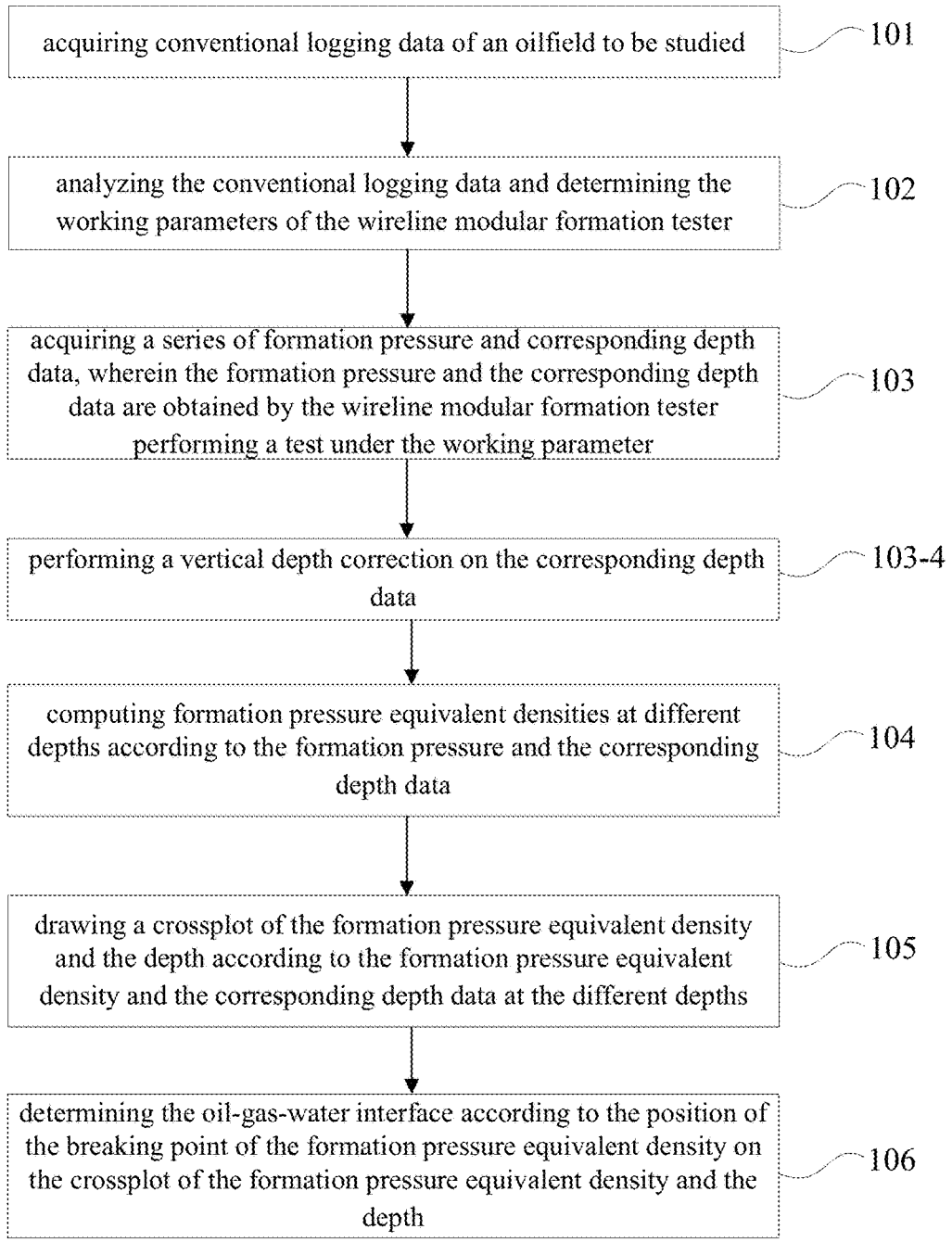
FIG. 3 is a flowchart (2) of a method for determining the oil-gas-water interface based on the formation pressure equivalent density provided in an embodiment of the present invention.

Based on the above, as shown in FIG. 3, the method for determining the oil-gas-water interface based on the formation pressure equivalent density further comprises:

step 103-4: performing a vertical depth correction on the corresponding depth data.

The method for performing the vertical depth correction specifically comprises the following acts: correcting the corresponding depth data point by point based on the hole angle of inclination in the conventional logging data.

Herein, the correction formula is shown as follows:

$$TVD = \int_0^{Depth} \cos(DEV(h))dh \quad (1)$$

wherein, TVD denotes the vertical depth, h denotes a well depth parameter, h is within a range from 0 to Depth, Depth denotes the logging depth, DEV denotes the hole angle of inclination, and dh denotes the depth sampling interval.

Figure 4:
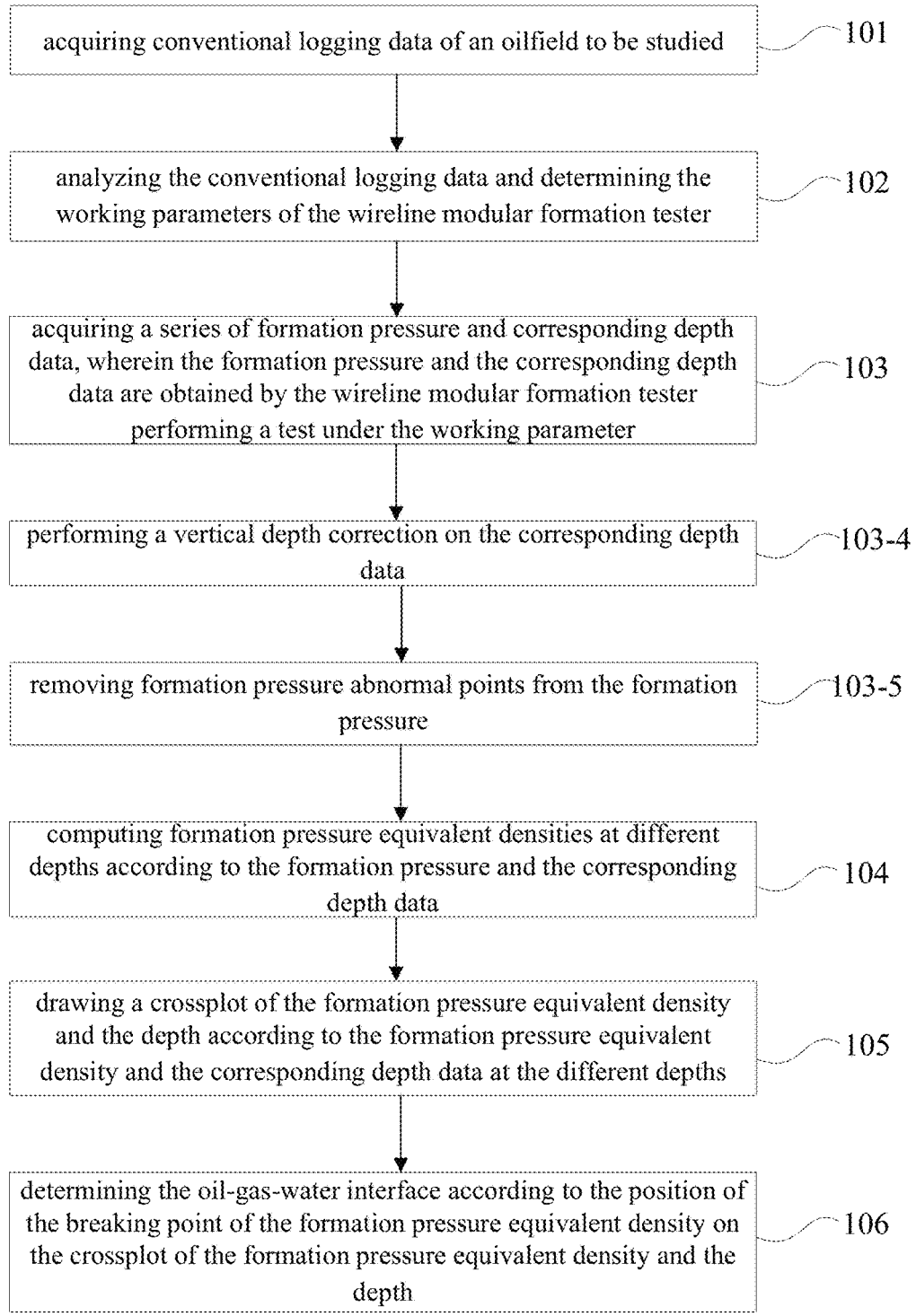
FIG. 4 is a flowchart (3) of the method for determining an oil-gas-water interface based on the formation pressure equivalent density provided in an embodiment of the present invention.

In the embodiments of the present invention, after the wireline modular formation tester is sealed by a rubber seat, a probe performs the single-point measurement. One problem that the obtained formation pressure data is not accurate sometimes appears due to the loss of seal, low fluidity of formation fluid, overpressure phenomenon and so on. The pressure values at these points cannot represent the actual pressure values of these points in the oil and gas reservoir, and in view of this, as shown in FIG. 4, the method for determining the oil-gas-water interface based on the formation pressure equivalent density further comprises:

step 103-5: removing formation pressure abnormal points from the formation pressure. Specifically, the removing procedure is performed by referring to the well logging interpretation report of modular formation tester (MDT) and the conventional logging data.

In embodiments of the present invention, in step 104, the formation pressure equivalent density is calculated by dividing the formation pressure by the depth and then by a coefficient, as shown in formula (2):

$$Q = P/\alpha M \quad (2)$$

Wherein, Q denotes the formation pressure equivalent density, g/cm³; P denotes the formation pressure, MPa or psi; M denotes a depth, m; α denotes a coefficient, the value of which depends on the unit of the formation pressure P, when the unit of P is MPa, the value of the coefficient is 0.0098, and when the unit of P is psi, the value of the coefficient is 1.422.

In the embodiments of the present invention, in step 105, the pressure equivalent density is taken as an X-axis, and the depth after the vertical depth correction is taken as a Y-axis, thereby obtaining a crossplot of the pressure equivalent density and the depth.

In the embodiments of the present invention, in step 106, in the gas layer that the pressure equivalent density value Q decreases with the increase of the depth M, i.e., Q is negatively correlated with M; in the oil layer, Q is also negatively correlated with M, but the change rate is smaller than that of the gas layer, this leads to a breaking point of Q at the interface between the gas layer and the oil layer; and in the upper and middle portions of an oil-water layer, Q is also negatively correlated with M, and the change rate is smaller than that of the oil layer, which also leads to a breaking point at the interface between the oil-water layer and the oil layer. A special phenomenon will appear at the lower portion of the oil-water layer: the relationship between Q and M changes from negative correlation to positive correlation, that is to say, an inflection point occurs, and it is generally considered that the parts above the inflection point is the oil-gas layer with commercial exploitation value. In a water layer, Q is basically unchanged or slightly positively correlated with the increase of depth M.

In embodiments of the present invention, the method also comprises:

setting an oil layer above the oil-water interface or a gas layer above the gas-water interface as the perforated interval;

performing a perforating operation, a hydraulic fracturing operation and/or an oil test operation to the perforated interval to obtain the produced liquid;

checking the accuracy of the oil-gas-water interface based on the proportion of the oil or gas in the produced liquid.

The purpose of hydraulic fracturing in perforated intervals is to increase the permeability of the oil or gas layers.

In the embodiments of the present invention, the method also comprises determining that a divided oil-gas-water interface is correct and transferring a well to the production stage when the proportion of oil or gas in the produced liquid exceeds 50%, and the oil and gas production reaches an industrial oil flow standard.

Next, specific implementations of the present invention will be further described in detail with reference to the accompanying drawings.

1. Collect conventional well logging data and logging data of the wireline modular formation tester (MDT) of research block. The formation pressure and corresponding depth data measured by MDT are extracted.

According to the conventional logging data and the comprehensive analysis of the drilling geological design report of the well X1 (FIG. 5), it is necessary to test the well section at 4680-4715 m for two purposes: firstly, for the well section at 4699.5-4704 m, further determine the fluid property of the section 4699.5-4704 m which is interpreted as oil-gas layer by conventional logging data; secondly, determine the oil-water interface accurately. For these purposes, points selection and design of MDT are performed, as shown in Table 1.

TABLE 1

Design of MDT Pressure Measurement and Sampling for X1 Well

| Depth point (m) | Test items | Purpose of test |
|---|---|---|
| 4691.5 | measuring pressure | Obtaining formation pressure |
| 4693 | measuring pressure | Obtaining formation pressure |
| 4693 | measuring pressure | Obtaining formation pressure |
| 4695 | measuring pressure | Obtaining formation pressure |
| 4695.5 | measuring pressure | Obtaining formation pressure |
| 4696 | measuring pressure | Obtaining formation pressure |
| 4696.5 | measuring pressure | Obtaining formation pressure |
| 4697 | measuring pressure | Obtaining formation pressure |
| 4700 | measuring pressure | Obtaining formation pressure |
| 4701 | measuring pressure + sampling | Obtaining formation fluid properties |
| 4702 | measuring pressure | Obtaining formation pressure |
| 4702.5 | measuring pressure | Obtaining formation pressure |
| 4703.5 | measuring pressure + sampling | Obtaining formation fluid properties |
| 4705 | measuring pressure | Obtaining formation pressure |
| 4706.5 | measuring pressure | Obtaining formation pressure |
| 4707 | measuring pressure | Obtaining formation pressure |
| 4708 | measuring pressure | Obtaining formation pressure |
| 4709.5 | measuring pressure | Obtaining formation pressure |

2. Make a vertical depth correction on the logging depth data For the well X1, no vertical depth correction is required when the hole angle of inclination does not exceed 1 degree. The deviation correction must be performed in the case of high-inclination well.

3. Remove abnormal points of formation pressure caused by the seal loss of instrument, formation densification, formation overpressure and other conditions.

Referring to two items of "Reservoir Fluidity" and "Pressure Measurement Evaluation" in Table 2, due to seal loss of instrument, formation densification, formation overpressure and other reasons, the values of some points cannot represent the true pressure value of the formation at this place, which will affect the analysis and calculation, so it should be removed at first. Five overpressure points and seven low fluidity points in the well X1 are removed. The depths corresponding to the five overpressure points are 4692 m, 4693 m, 4694 m, 4695.5 m and 4697 m respectively, and the seven low fluidity points are 4691.6 m, 4691.8 m, 4692.2 m, 4695 m, 4696 m, 4696.5 m and 4696.7 m, respectively.

TABLE 2

Table of Logging Data of MDT Single Well
Borehole type: Value well Maximum well inclination (°): 1 Drill bit diameter (mm): 215.9 Mud density (g/cm³): 1.2 Water loss of mud: 1.8 Bottom hole temperature (°): 110 Reservoir lithology: Sand mudstone

| | Pressure measuring | | | | | | |
|---|---|---|---|---|---|---|---|
| Depth of measuring point (m) | Mud Column Pressure (PSI) | Formation pressure (PSI) | Reservoir Fluidity (md/cp) | Time for pressure measuring (min) | Pressure Measurement Evaluation | Type of pressure measuring probe | Type of pumping probe |
| 4691.4 | | | — | | Drying point | XLDP | |
| 4691.6 | | | 0.03 | | Fluidity measuring | XLDP | |
| 4691.8 | | | 0.03 | | Fluidity measuring | XLDP | |

TABLE 2-continued

Table of Logging Data of MDT Single Well
Borehole type: Value well  Maximum well inclination (°): 1  Drill bit diameter (mm): 215.9  Mud density
(g/cm³): 1.2  Water loss of mud: 1.8  Bottom hole temperature (°): 110  Reservoir lithology: Sand mudstone

| | | | | | | | |
|---|---|---|---|---|---|---|---|
| 4692 | 8328.9 | 7703.4 | 0.03 | | Overpressure | XLDP | |
| 4692.2 | | | 0.06 | | Fluidity measuring | XLDP | |
| 4693 | 8290.7 | 7399.0 | <0.01 | | Overpressure | XLDP | |
| 4694 | 8300.3 | 7367.0 | <0.01 | | Overpressure | XLDP | |
| 4695 | | | <0.1 | | Fluidity measuring | XLDP | |
| 4695.5 | 8309.0 | 7436.0 | 0.01 | | Overpressure | XLDP | |
| 4696 | 8322.0 | 7366.0 | 0.03 | | Fluidity measuring | XLDP | |
| 4696.5 | 8314.0 | 7328.0 | 0.2 | | Fluidity measuring | XLDP | |
| 4696.7 | 8339.0 | 7328.5 | 0.2 | | Fluidity measuring | XLDP | |
| 4697 | 8371.0 | 7343.6 | 0.5 | | Overpressure | XLDP | |
| 4700 | 8337.0 | 7300.2 | 37.6 | | Normal | XLDP | |
| 4701.3 | 8342.0 | 7301.4 | 6.5 | 8 | Normal | XLDP | XLDP |
| 4702 | 8344.6 | 7302.3 | 1.5 | 8 | Normal | XLDP | |
| 4702.5 | 8340.8 | 7302.9 | 68.3 | 15 | Normal | XLDP | |
| 4703.5 | 8349.0 | 7304.2 | 16.2 | 8 | Normal | XLDP | XLDP |
| 4704.9 | 8353.4 | 7306.1 | 58.4 | 6 | Normal | XLDP | |
| 4706.4 | 8357.7 | 7308.3 | 65.9 | 7 | Normal | XLDP | |
| 4707 | 8360.0 | 7309.3 | 51.4 | 9 | Normal | XLDP | |
| 4708 | 8361.8 | 7310.8 | 56.5 | 7 | Normal | XLDP | |
| 4709.5 | 8363.0 | 7313.1 | 132.5 | 8 | Normal | XLDP | |

| | Fluid analysis related data (LFA/CFA) | | | | | | |
|---|---|---|---|---|---|---|---|
| Depth of measuring point (m) | Application module | Pumping time (min) | Pumping fluid (liter) | Analysis of fluid composition | | | Test evaluation |
| | | | | Gas-containing | Oil-containing | Water-containing | |
| 4691.4 | | | | | | | |
| 4691.6 | | | | | | | |
| 4691.8 | | | | | | | |
| 4692 | | | | | | | |
| 4692.2 | | | | | | | |
| 4693 | | | | | | | |
| 4694 | | | | | | | |
| 4695 | | | | | | | |
| 4695.5 | | | | | | | |
| 4696 | | | | | | | |
| 4696.5 | | | | | | | |
| 4696.7 | | | | | | | |
| 4697 | | | | | | | |
| 4700 | | | | | | | |
| 4701.3 | LFA | 422 | 151 | 5% | 45% | 50% | Normal |
| 4702 | | | | | | | |
| 4702.5 | | | | | | | |
| 4703.5 | LFA | 401 | 186 | Small amount | 5% | 95% | Normal |
| 4704.9 | | | | | | | |
| 4706.4 | | | | | | | |
| 4707 | | | | | | | |
| 4708 | | | | | | | |
| 4709.5 | | | | | | | |

4. Calculate the formation pressure equivalent density point by point

Referring to Table 2, the formation pressure equivalent density is calculated after removing abnormal data points; because the existing wireline testing instruments generally use psi as the unit of pressure, the coefficient α should be selected to be 1.422, then the calculated formation pressure equivalent density should be in the unit of g/cm³. Taking the point at depth of 4720 m as an example, the formation pressure at this point is 7302.3 psi, so that the formation pressure equivalent density calculated therefrom should be 1.092138 g/cm³.

5. Draw the crossplot of formation pressure equivalent density and depth

Figure 6:
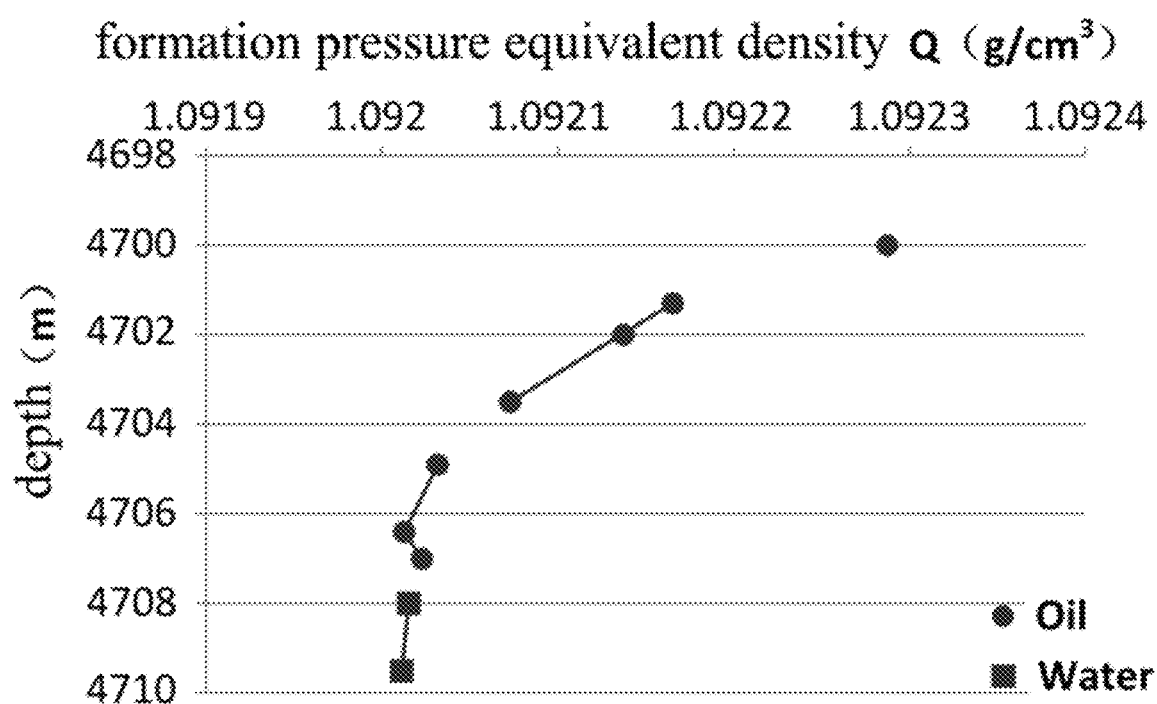
FIG. 6 is a crossplot of formation pressure equivalent density and depth of a well X1 provided in an embodiment of the present invention.

The valid formation pressure equivalent density Q and corresponding depth M of the well X1 are extracted, and a crossplot is made by taking Q as a horizontal coordinate and M as a longitudinal coordinate, see FIG. 6. It should be noted that different reservoir sections and different pressure systems should be plotted separately. Due to the small change of Q, i.e., the formation pressure equivalent density usually changes after two decimal places, it is necessary to accurately select the range of the horizontal coordinate. In the well X1, the Q value of the oil-gas layer descends from 1.09229 g/cm³ (at the depth 4700 mm) to 1.09207 g/cm³ (at the depth 4703.5 m). The absolute value of the descending is 0.00022 g/cm3, and the relative value thereof is 0.00006 g/cm 3/m.

6. The oil-gas-water reservoir is divided according to the position of the breaking point of the formation pressure equivalent density Q on the crossplot.

Figure 5:
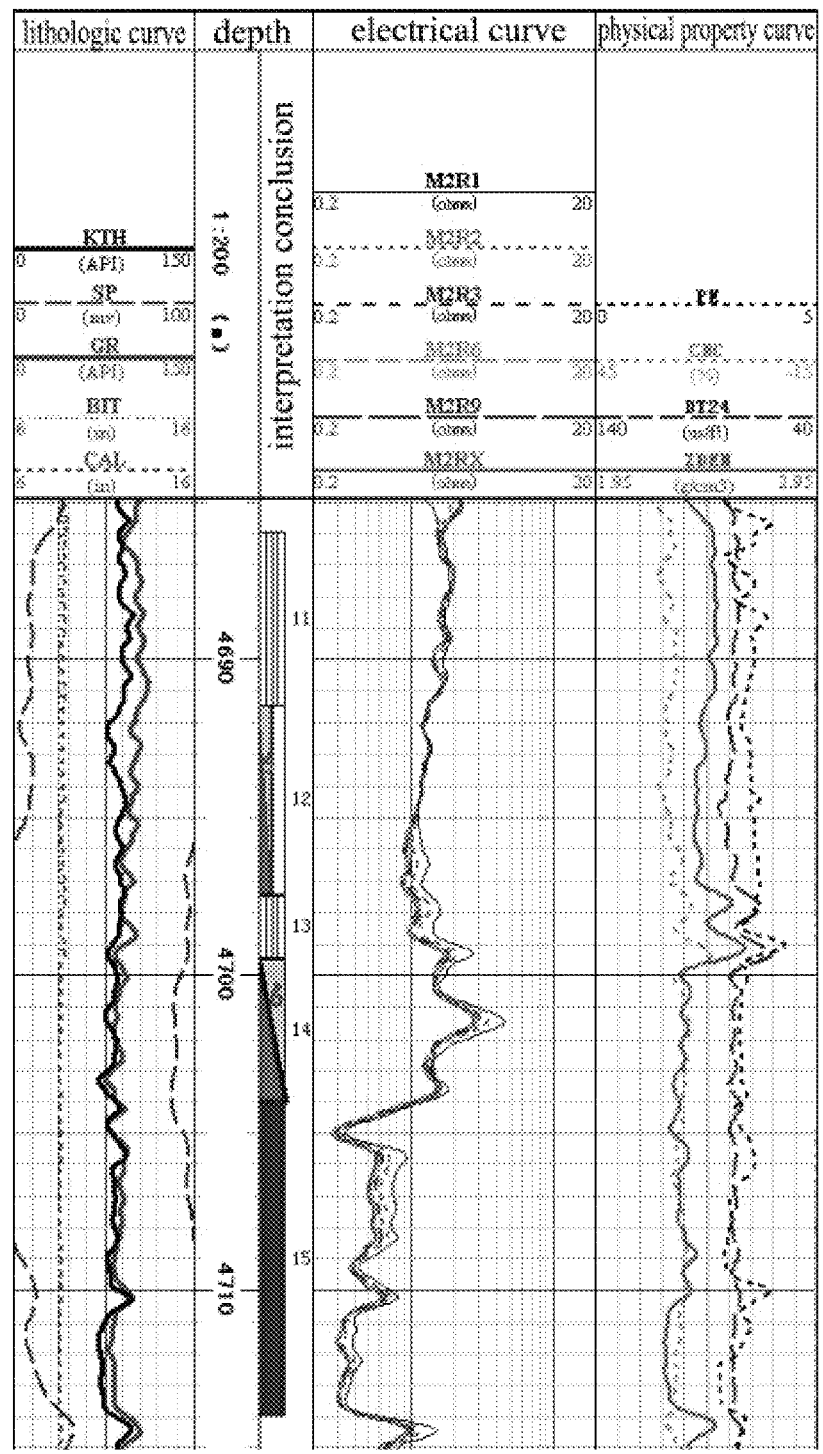
FIG. 5 is a diagram of conventional logging interpretation results of a well X1 provided in an embodiment of the present invention.

As can be seen from the logging interpretation results of the well X1 as shown in FIG. 5, the first column (lithologic curves) includes totally five curves of uranium removal gamma (KTH), spontaneous potential (SP), natural gamma (GR), bit size (BIT) and well diameter (CAL); the third column (electrical curves) includes six resistivity curves representing different radial probe depths; and the fourth column (physical property curves) includes totally four curves of a photoelectric cross section (PE), neutron porosity (CNC), P-wave slowness (DT24) and formation density (ZDEN). Through comprehensive analysis of the above logging data, it can be concluded that the depth section at 4700 m-4704 m is an oil layer and the depth section at 4704 m-4713.9 m is a water layer. Again as can be seen from the crossplot of formation pressure equivalent density Q and depth M shown in FIG. 6, Q of the depth section at 4700 m-4703.5 m is negatively correlated with M; Q of the depth section at 4704.9 m-4706.4 m is still negatively correlated with M, but the change range of Q decreases; an inflection point appears at the depth of 4706.4 m, Q of the depth section at 4706.4 m-4707 m is positively correlated with M; Q of the depth section at 4708 m-4709.6 m is basically unchanged along with the change of M. According to the analysis, it can be concluded that the depth section at 4700 m-4703.5 m is an oil layer, the depth section at 4704.9 m-4706.4 m is an oil-water layer that has commercial exploration value and a high oil saturation, the depth section at 4706.4 m-4707.7 m is an oil-containing water layer without exploration value, and the depth section at 4708 m-4709.6 m is a water layer. As can be seen from comparison between the crossplot and the logging interpretation results, the method described in the present invention moves the oil-water interface judged by the logging interpretation downwards from 4704 m to 4706.4 m, which increases the thickness of the oil-gas layer or the oil-water layer that has commercial exploration value.

Figure 7:
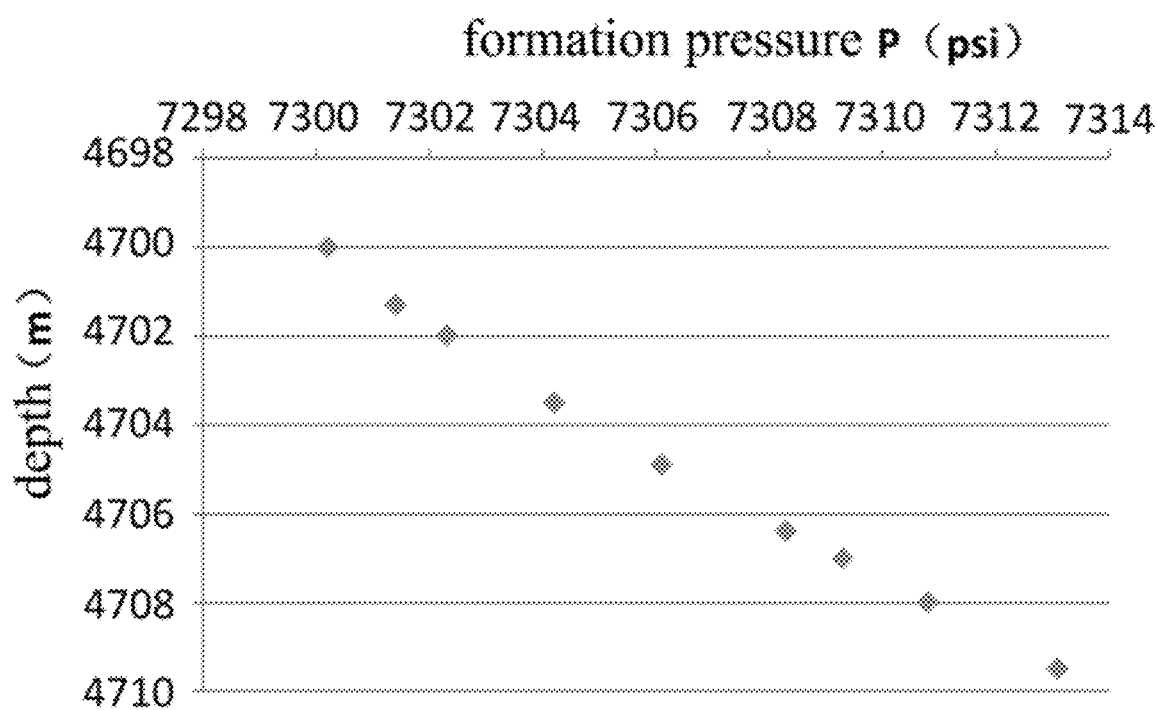
FIG. 7 is a crossplot of formation pressure and depth of a well X1 that is obtained by using a traditional method.

FIG. 7 is a crossplot of the formation pressure and the depth, which is a conventional method for determining the oil-gas-water interface according to the changing relationship between formation pressure and depth. In the crossplot, it is difficult to identify three layers: an oil layer, an oil-water layer and a water layer. In contrast, the method for determining the oil-gas-water interface based on the formation pressure equivalent density provided in the present invention is more advantageous.

The embodiments of the present invention also provide a computer-readable storage medium, where the computer-readable storage medium stores a computer program for implementing the following steps: acquiring conventional logging data of an oilfield to be studied; analyzing the conventional logging data and determining working parameters of the wireline modular formation tester; acquiring a series of formation pressure and corresponding depth data, wherein the formation pressure and the corresponding depth data are obtained by the wireline modular formation tester performing a test under the working parameter; computing formation pressure equivalent densities at different depths according to the formation pressure and the corresponding depth data; drawing a crossplot of the formation pressure equivalent density and the depth according to the formation pressure equivalent density and the corresponding depth data at different depths; determining the oil-gas-water interface according to the position of the breaking point of the formation pressure equivalent density on the crossplot of the formation pressure equivalent density and the depth.

Herein, the computer program is used for implementing the following step of: performing a vertical depth correction on the corresponding depth data.

Herein, the computer program is used for implementing the step of performing a vertical depth correction on the corresponding depth data by: determining hole angle of inclination in conventional logging data; and performing a vertical depth correction on the corresponding depth data according to the data of the hole angle of inclination.

Herein, according to the data of the hole angle of inclination, the vertical depth correction is performed on the corresponding depth data by using the formula (1).

Herein, the computer program is used for implementing the following: removing formation pressure abnormal points from the formation pressure.

Herein, formation pressure equivalent densities of different depths are determined in accordance with the formula (2) based on the formation pressure and the corresponding depth data.

Herein, the computer program can be used for implementing the following: setting the oil layer above the oil-water interface or the gas layer above the gas-water interface as the perforated interval; performing a perforating operation, hydraulic fracturing operation and/or oil test operation to the perforated interval to obtain the produced liquid; and checking the accuracy of the oil-gas-water interface based on the proportion of the oil or gas in the produced liquid.

The computer program can also be used for implementing the following: when the proportion of oil or gas in the produced liquid exceeds 50%, and the oil and gas production reaches the industrial oil flow standard, it is determined that the divided oil-gas-water interface is correct, and the well is transferred to the production stage.

The computer-readable storage medium may include physical means for storing information, and the physical means may digitize and then store information by a medium using electrical, magnetic or optical means. The computer-readable storage medium according to the present embodiment may include an apparatus for storing information in an electric energy manner, e.g., various types of memories such as RAM, ROM, or the like; an apparatus for storing information by means of magnetic energy, such as a hard disk, a floppy disk, a magnetic tape, a magnetic core memory, a bubble memory, a U disk, or the like; an apparatus for storing information optically, such as a CD, a DVD, or the like. Of course, there are other kinds of readable storage media, such as a quantum memory, a graphene memory, or the like.

In conclusion, the method and the apparatus for determining the oil-gas-water interface based on the formation pressure equivalent density provided by the present invention have the following beneficial effects.

The formation pressure equivalent densities at different depths are determined through the formation pressure and corresponding depth data in the logging data of the wireline modular formation tester, then a crossplot of the formation pressure equivalent density and the depth is drawn according to the formation pressure equivalent density and the corresponding depth data at the different depths, and the oil-gas-water interface is determined according to the position of the breaking point of the formation pressure equivalent density on the crossplot of the formation pressure equivalent density and the depth. In this way, a rate of identification of low resistance reservoir, heavy oil reservoir and low porosity and low permeability oil and gas reservoir in the exploration stage can be improved, and the division of the oil-gas-water layer is more accurate, so as to provide a scientific basis for the deployment and planning of oil and gas exploration schemes.

Persons skilled in the art shall understand that, the embodiments of the present invention can be provided as a method, a system or a computer program product. Therefore, the present invention can adopt the forms of a full hardware example, a full software example, or combination of a software example and a hardware example. Moreover, the present invention can adopt the form of a computer program product that is implemented on one or more computer-usable storage medium (including but not limited to a disk memory, a CD-ROM, an optical memory, and etc.) including computer-usable program codes.

The invention is described with reference to flowcharts and/or block diagrams of the method, the device (system) and the computer program product according to the embodiments of the invention. It should be understood that each flow and/or block in the flowcharts and/or block diagrams, and the combination of the flows and/or blocks in the flowcharts and/or block diagrams can be achieved by computer program instructions. These computer program instructions can be provided to a CPU of a general-purpose computer, a special-purpose computer, an embedded processor or other programmable data processing device to produce a machine, so that a device for achieving functions designated in one or more flows in the flowcharts and/or one or more blocks in the block diagrams can be generated by the instructions executed by the CPU of the computer or other programmable data processing device.

These computer program instructions can also be stored in a computer-readable memory that can guide a computer or other programmable data processing device to operate in a special way, so that the instructions stored in the computer-readable memory generate a manufactured product including an instruction apparatus which achieves functions designated in one or more flows in the flowcharts and/or one or more blocks in the block diagrams.

These computer program instructions can also be loaded on a computer or other programmable data processing devices, on which a series of operation steps are executed to generate processes achieved by the computer, so that the instructions executed on the computer or other programmable data processing devices is provided for being used in the steps of achieving functions designated in one or more flows in the flowcharts and/or one or more blocks in the block diagrams.

The foregoing is merely preferred embodiments of the present invention and is not intended to limit the present invention. Various modifications and variations can be made to the embodiments of the present invention by those skilled in the art. Any modifications, equivalents, improvements, etc. made within the spirit and principle of the present invention are intended to be included within the protection scope of the present invention.

The invention claimed is:

1. A method for determining an oil-gas-water interface based on formation pressure equivalent density, wherein the method comprises the steps of:
   acquiring conventional logging data of an oilfield well to be studied;
   analyzing the conventional logging data and determining working parameters of a wireline modular formation tester;
   acquiring a series of formation pressure and corresponding depth data, wherein the formation pressure and the corresponding depth data are obtained by the wireline modular formation tester performing a test under the working parameters;
   computing formation pressure equivalent densities at different depths according to the formation pressure and the corresponding depth data by:

$$Q=P/\alpha M;$$

wherein, Q denotes a formation pressure equivalent density, g/cm$^3$; P denotes a formation pressure, in MPa or psi; M denotes a depth, m; $\alpha$ denotes a coefficient that is dependent on the unit of the formation pressure P, when the unit of P is MPa, the value of $\alpha$ is 0.0098, and when the unit of P is psi, the value of a is 1.422;
   drawing a crossplot of the formation pressure equivalent density and the depth according to the formation pressure equivalent density and the corresponding depth data at the different depths; and
   determining an oil-gas-water interface according to a position of a breaking point of the formation pressure equivalent density on the crossplot of the formation pressure equivalent density and the depth.

2. The method for determining the oil-gas-water interface based on the formation pressure equivalent density according to claim 1, wherein the method further comprises a step of:
   performing a vertical depth correction on the corresponding depth data.

3. The method for determining the oil-gas-water interface based on the formation pressure equivalent density according to claim 2, wherein the step of performing the vertical depth correction on the corresponding depth data is implemented by:
   determining data of hole angle of inclination in the conventional logging data; and
   performing the vertical depth correction on the corresponding depth data according to the data of the hole angle of inclination.

4. The method for determining the oil-gas-water interface based on the formation pressure equivalent density according to claim 3, wherein the step of performing the vertical depth correction on the corresponding depth data according to the data of the hole angle of inclination is implemented by:

$$TVD=\int_0^{Depth} \cos(DEV(h))dh;$$

wherein, TVD denotes a vertical depth, h denotes a well depth parameter within a range from 0 to Depth, Depth denotes the logging depth, DEV denotes data of the hole angle of inclination, and dh denotes a depth sampling interval.

5. The method for determining the oil-gas-water interface based on the formation pressure equivalent density according to claim 1, wherein the method further comprises a step of:
   removing formation pressure abnormal points from the formation pressure.

6. The method for determining the oil-gas-water interface based on the formation pressure equivalent density according to claim 1, wherein the method further comprises:
   setting an oil layer above an oil-water interface or a gas layer above a gas-water interface as a perforated interval;
   performing a perforating operation, a hydraulic fracturing operation and an oil test operation to the perforated interval to obtain a produced liquid;
   checking the accuracy of the oil-gas-water interface based on a proportion of the oil or gas in the produced liquid.

7. The method for determining the oil-gas-water interface based on the formation pressure equivalent density according to claim 6, wherein the method further comprises:
   when the proportion of oil or gas in the produced liquid of a well exceeds 50%, and the oil and gas production reaches an industrial oil flow standard, it is determined that a divided oil-gas-water interface is correct, and the well is transferred to a production stage.

8. A computer-readable storage medium, wherein the computer-readable storage medium stores a computer program for implementing the following steps:

acquiring conventional logging data of an oilfield to be studied;

analyzing the conventional logging data and determining working parameters of a wireline modular formation tester;

acquiring a series of formation pressure and corresponding depth data, wherein the formation pressure and the corresponding depth data are obtained by the wireline modular formation tester performing a test under the working parameter;

computing formation pressure equivalent densities at different depths according to the formation pressure and the corresponding depth data by:

$$Q = P/\alpha M;$$

wherein, Q denotes a formation pressure equivalent density, g/cm³; P denotes a formation pressure, in MPa or psi; M denotes a depth, m; α denotes a coefficient that is dependent on the unit of the formation pressure P, when the unit of P is MPa, the value of α is 0.0098, and when the unit of P is psi, the value of α is 1.422;

drawing a crossplot of the formation pressure equivalent density and the depth according to the formation pressure equivalent density and the corresponding depth data at the different depths; and determining an oil-gas-water interface according to a position of a breaking point of the formation pressure equivalent density on the crossplot of the formation pressure equivalent density and the depth.

9. The computer-readable storage medium according to claim 8, wherein the computer program is used for implementing the following step of:

performing a vertical depth correction on the corresponding depth data.

10. The computer-readable storage medium according to claim 9, wherein the computer program is used for implementing the step of performing a vertical depth correction on the corresponding depth data by:

determining data of the hole angle of inclination in the conventional logging data; and performing the vertical depth correction on the corresponding depth data according to the data of the hole angle of inclination.

11. The computer-readable storage medium according to claim 10, wherein the computer program is used for implementing the step of performing the vertical depth correction on the corresponding depth data according to the data of the deviation angle by:

$$TVD = \int_0^{Depth} \cos(DEV(h))dh;$$

wherein, TVD denotes the vertical depth, h denotes a well depth parameter within a range from 0 to Depth, Depth denotes the logging depth, DEV denotes data of the hole angle of inclination, and dh denotes the depth sampling interval.

12. The computer-readable storage medium according to claim 8, wherein the computer program is used for implementing the following:

removing formation pressure abnormal points in the formation pressure.

13. The computer-readable storage medium according to claim 8, wherein the computer program is used for implementing the following:

setting an oil layer above an oil-water interface or a gas layer above a gas-water interface as a perforated interval;

performing a perforating operation, hydraulic fracturing operation and oil test operation to the perforated interval to obtain a produced liquid;

checking the accuracy of the oil-gas-water interface based on a proportion of the oil or gas in the produced liquid.

14. The computer-readable storage medium according to claim 13, wherein the computer program is used for implementing the following:

when the proportion of oil or gas in the produced liquid of a well exceeds 50%, and the oil and gas production reaches an industrial oil flow standard, it is determined that a divided oil-gas-water interface is correct, and the well is transferred to a production stage.

* * * * *